US00PP27130P2

(12) United States Plant Patent
Sills et al.

(10) Patent No.: US PP27,130 P2
(45) Date of Patent: Sep. 6, 2016

(54) BLACKBERRY PLANT NAMED 'DRISBLACKFIFTEEN'

(50) Latin Name: ***Rubus* L. subgenus *Rubus***
Varietal Denomination: DrisBlackFifteen

(71) Applicant: DRISCOLL STRAWBERRY ASSOCIATES, INC., Watsonville, CA (US)

(72) Inventors: Gavin R. Sills, Gilroy, CA (US); Andrea M. Pabon, Gilroy, CA (US); Mark Crusha, Capitola, CA (US)

(73) Assignee: Driscoll Strawberry Associates, Inc., Watsonville, CA (US)

( * ) Notice: Subject to any disclaimer, the term of this patent is extended or adjusted under 35 U.S.C. 154(b) by 8 days.

(21) Appl. No.: 14/544,850

(22) Filed: Feb. 25, 2015

(51) Int. Cl.
*A01H 5/08* (2006.01)

(52) U.S. Cl.
USPC ..... Plt./203

(58) Field of Classification Search
USPC ..... Plt./203
CPC ..... A01H 5/0887
See application file for complete search history.

*Primary Examiner* — Kent L Bell
(74) *Attorney, Agent, or Firm* — Morrison & Foerster LLP

(57) ABSTRACT

This invention relates to a new and distinct variety of blackberry plant named 'DrisBlackFifteen', particularly characterized by having medium to high vigor, medium to large-sized, black berries and self-fruitful plants, is disclosed.

2 Drawing Sheets

Genus and species: *Rubus* L. subgenus *Rubus*.
Variety denomination: 'DrisBlackFifteen'.

BACKGROUND OF THE NEW PLANT

The present invention relates to a new and distinct blackberry cultivar designated 'DrisBlackFifteen' and botanically known as *Rubus* L. subgenus *Rubus*. This new blackberry variety was identified in Santa Cruz County, Calif. in July 2005 and originated from a cross between the proprietary female parent blackberry plant 'BF745.1' (unpatented) and the proprietary male parent blackberry plant 'BE543.2' (unpatented). The original seedling of the new cultivar was first asexually propagated by tissue culture and root cuttings at a nursery in Santa Cruz County, Calif. in 2005. 'DrisBlackFifteen' was subsequently asexually propagated by tissue culture and root cuttings and underwent further testing at a nursery in Santa Cruz County, Calif. from 2005 to 2014. The present invention has been found to be stable and reproduce true to type through successive asexual propagations.

Plant Breeder's Rights for this variety have not been applied for. 'DrisBlackFifteen' has not been made publicly available or sold anywhere in the world more than one year prior to the filing date of this application.

SUMMARY OF THE INVENTION

The following are the most outstanding and distinguishing characteristics of this new cultivar when grown under normal horticultural practices in Santa Cruz County, Calif.

1. Medium to high vigor;
2. Medium to large sized, black berries; and
3. Self-fruitful plants.

DESCRIPTION OF THE PHOTOGRAPHS

This new blackberry plant is illustrated by the accompanying photographs which show the plant's canes, flowers, fruit, and leaves. The colors shown are as true as can be reasonably obtained by conventional photographic procedures. The photographs are of plants that are 3 years old.

Figure 1:
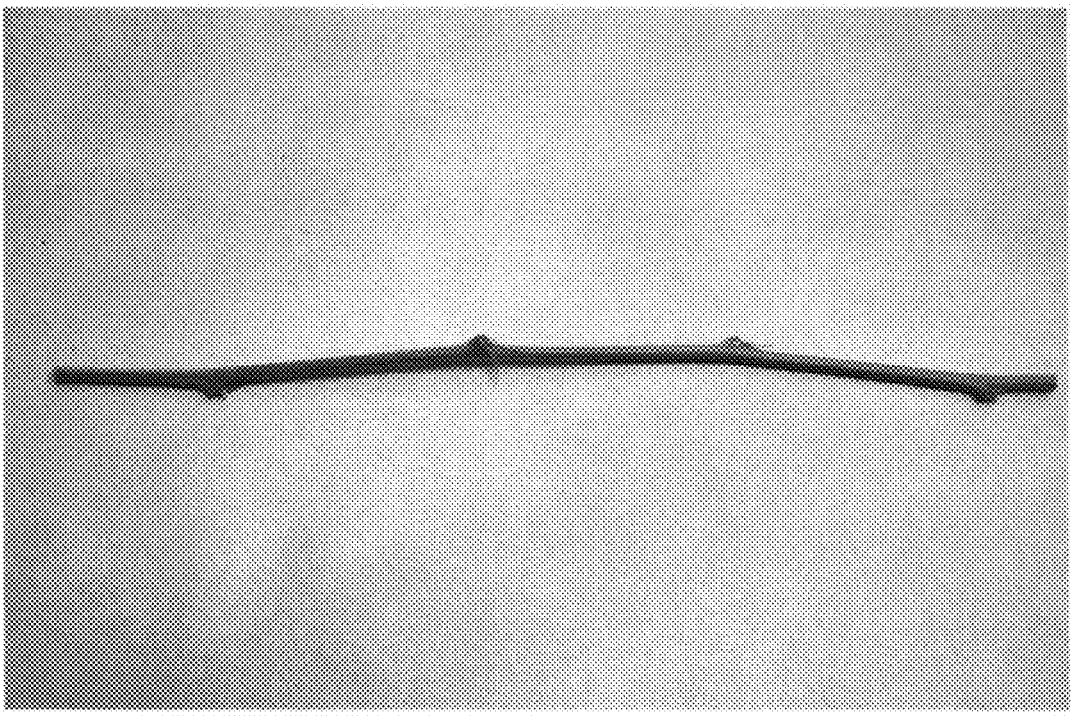
Figure 2:
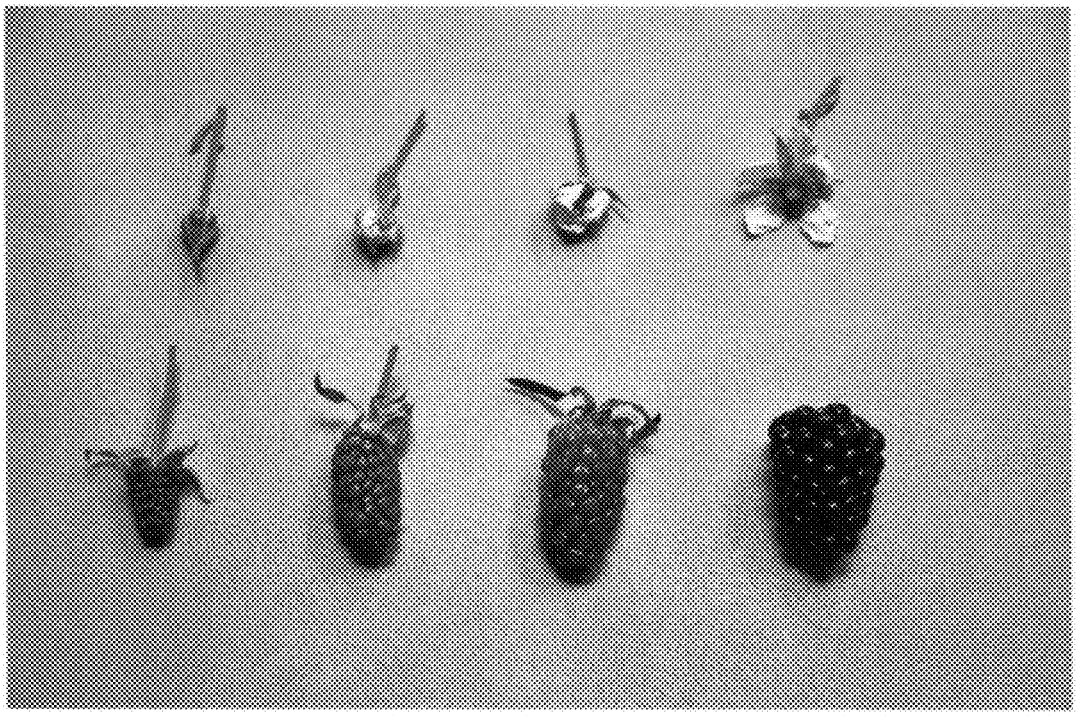
Figure 3:
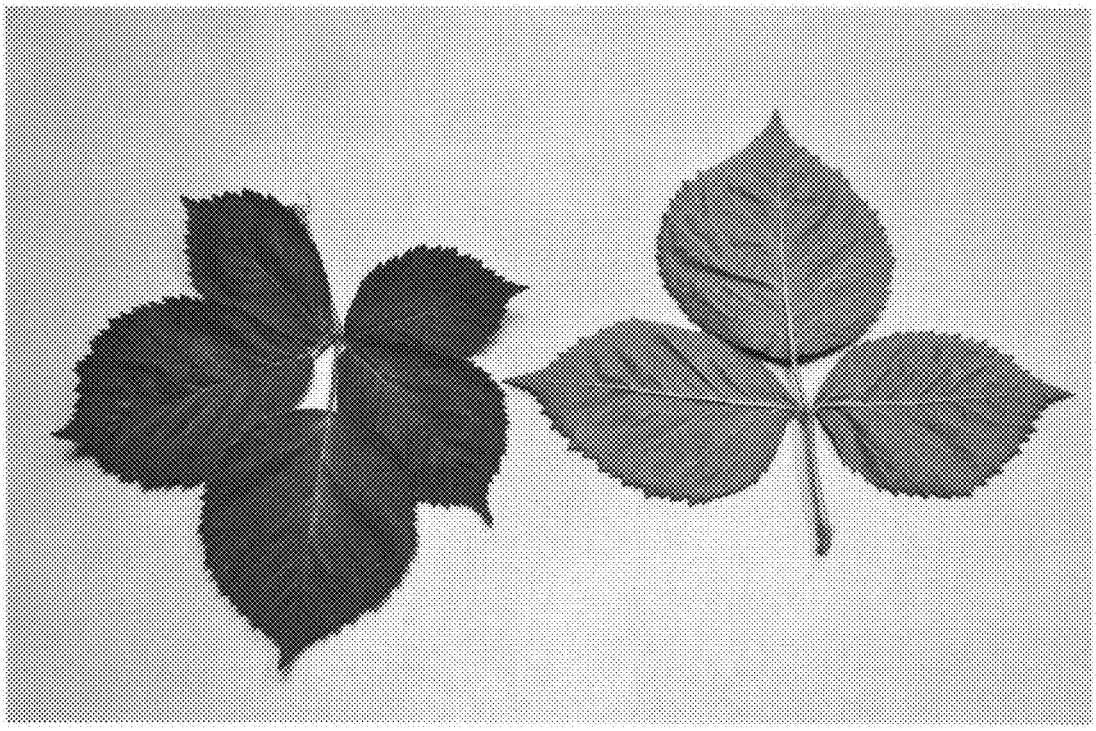

FIG. 1 shows a section of a young cane without spines.
FIG. 2 shows the flowers and fruit at various stages.
FIG. 3 shows the upper and lower surfaces of the leaves.

DESCRIPTION OF THE NEW VARIETY

The following descriptions of 'DrisBlackFifteen' are based on observations made in Santa Cruz County, Calif. on 3-year old plants. This description is in accordance with UPOV terminology. Color designations, color descriptions, and other phenotypical descriptions may deviate from the stated values and descriptions depending upon variation in environmental, seasonal, climatic and cultural conditions. 'DrisBlackFifteen' has not been observed under all possible environmental conditions. Color terminology follows The Royal Horticultural Society Colour Chart, London (R.H.S.) (2007 edition). Descriptive terminology is from the *Plant Identification Terminology, An Illustrated Glossary* 2$^{nd}$ edition, by James G. Harris and Melinda Woolf Harris, unless where otherwise defined.

DETAILED BOTANICAL DESCRIPTION

Classification:
*Family*.—Rosaceae.
*Botanical*.—*Rubus* L. subgenus *Rubus*.
*Common name*.—Blackberry.
*Variety name*.—'DrisBlackFifteen'.

Parentage:
*Female parent*.—Proprietary blackberry plant named 'BF745.1' (unpatented).
*Male parent*.—Proprietary blackberry plant named 'BE543.2' (unpatented).

Plant:

*Vigor*.—Medium to high.

*Growth habit*.—Semi-upright.

*Productivity*.—Medium to high.

*Propagation*.—Tissue culture and root cuttings.

*Self-fruitfulness*.—Self-fruitful.

*Time of bud burst*.—Medium.

Canes:

*Fruiting lateral length* (4$^{th}$ *lateral from tip*).—Short to medium; 39.6 cm.

*Number of fruit per lateral*.—9.

*Fruiting on current year's cane*.—Absent.

*Cane internodal distance*.—8.1 cm.

*Number of new canes during flowering*.—Many.

*New cane strength* (*observed full-grown shoot after picking*).—Strong.

*Glaucosity observed on full-grown shoot after picking*.—Medium.

*Young shoots*.—Quantity: Few. Time of emergence from soil: Medium. Anthocyanin coloration (during rapid growth): Weak; RHS 178B (greyed-red). Intensity of green color: Medium; RHS 146C (yellow-green). Number of glandular hairs: Absent or few.

*Dormant cane*.—Length: Long. Diameter (in central third): Medium. Cross section (from mid cane observed at end of first growing season): Rounded. Number of branches: Medium. Distribution of branches: Over whole length. Anthocyanin coloration: Medium. Spines: Absent.

Leaves:

*Type*.—Palmate.

*Predominant number of leaflets*.—Three.

*Overlapping or relative position of lateral leaflet*.—Touching.

*Color*.—Upper surface: Medium; RHS 136A (green). Lower surface: Medium; RHS 139A (green).

*Glossiness of upper side*.—Weak.

*Cross section profile*.—Convex (margins rolled backwards).

*Leaflets*.—Shape: Oval. Margin: Doubly serrate. Depth of incisions: Medium. Type of incision margin: Biserrate. Apex: Truncate. Base: Obtuse. Rachis length between terminal leaflet and adjacent lateral leaflet: 24.7 mm.

*Lateral leaflet* (*basal pair*).—Length: 83.0 mm. Width: 66.3 mm. Length/width ratio: 1.3.

*Terminal leaflet*.—Length: Medium; 109.1 mm. Width: Medium; 65.3 mm. Length/width ratio: 1.7. Lobing: Absent. Undulation of margin (rippling of margin): Strong. Blistering between veins (rugosity): Weak to medium. Shape: Oval. Tip: Convex. Base: Obtuse. Margin: Doubly serrate. Cross-section: U-shaped.

*Petiole*.—Length: 6.7 mm. Diameter: 2.5 mm. Pigmentation: Upper surface: Lightly; RHS 138A (green). Lower surface: Lightly; RHS 143C (green).

*Stipule*.—Size: Large. Orientation: Erect.

Inflorescence:

*Flower diameter*.—Medium; 47.06 mm.

*Flower number* (*at* 3$^{rd}$ *node from tip of lateral*).—2.

*Petal*.—Length: 23.19 mm. Width: 14.23 mm. Length/width ratio: 1.6. Color: RHS N155B (White).

*Pedicel*.—Length: 31.49 mm. Diameter: 1.22 mm.

*Time of beginning of flowering on previous year's cane*.—Medium.

*Time of beginning of flowering on current year's cane*.—N/A.

Fruit:

*Size*.—Medium to large.

*Length*.—Long; 32.37 mm.

*Width*.—Medium; 23.65 mm.

*Ratio of length to width*.—Medium to large; 1.4.

*Weight* (*g/fruit*).—8.1 g.

*Soluble solids* (%) (*in Brix*).—11.8.

*Titratable acidity*: (% *as citric acid*).—0.92.

*Seed weight* (*g/seed*).—0.00831.

*Number of drupelets/fruit*.—Medium to many; 93.

*Size of drupelet*.—Medium to large.

*Color*.—Immature: RHS 138A (medium green). Maturing: RHS 185A (greyed-purple). Mature: RHS 203A (Black).

*Firmness*.—Medium.

*Glossiness*.—Medium.

*Shape in longitudinal section*.—Long conical.

*Time of ripening on previous year's cane*.—Medium to late.

*Time of ripening on current year's cane*.—N/A.

*Harvest interval*.—Mid-July to early September.

*Yield*.—Medium.

Disease, pest, and stress resistance: Not tested.

COMPARISON WITH PARENTAL AND COMMERCIAL VARIETIES

'DrisBlackFifteen' differs from the proprietary female parent 'BF745.1' (unpatented) in that 'DrisBlackFifteen' has higher yields than 'BF745.1'.

'DrisBlackFifteen' differs from the proprietary male parent 'BE543.2' (unpatented) in that 'DrisBlackFifteen' has higher yields and later production than 'BE543.2'.

'DrisBlackFifteen' differs from the commercial variety 'Driscoll Cowles' (U.S. Plant Pat. No. 14,780) in that 'DrisBlackFifteen' has long conical shaped fruit that is medium glossy, whereas 'Driscoll Cowles' has narrow ovate to long conical shaped fruit that is strongly glossy. Additionally, 'DrisBlackFifteen' has a medium to high vigor, whereas 'Driscoll Cowles' has high vigor.

'DrisBlackFifteen' differs from commercial variety 'DrisBlackTwo' (U.S. Plant Pat. No. 22,002) in that 'DrisBlackFifteen' has long conical shaped fruit that is medium glossy, whereas 'DrisBlackTwo' has ovate shaped fruit that is strongly glossy. Additionally, 'DrisBlackFifteen' has a medium yield, whereas 'DrisBlackTwo' has a high to very high yield.

We claim:

1. A new and distinct variety of blackberry plant named 'DrisBlackFifteen', substantially as illustrated and described herein.

* * * * *